(12) United States Patent
Larkins (10) Patent No.: US 7,067,158 B2
(45) Date of Patent: Jun. 27, 2006

(54) PREPARATION FOR THE RELIEF OF DISEASE

(75) Inventor: Nicholas J. Larkins, London (GB)

(73) Assignee: AKL Technologies Limited, London (GB)

( * ) Notice: Subject to any disclaimer, the term of this patent is extended or adjusted under 35 U.S.C. 154(b) by 16 days.

(21) Appl. No.: 10/398,110

(22) PCT Filed: Oct. 19, 2001

(86) PCT No.: PCT/GB01/04687

§ 371 (c)(1),
(2), (4) Date: Aug. 1, 2003

(87) PCT Pub. No.: WO02/32435

PCT Pub. Date: Apr. 25, 2002

(65) Prior Publication Data

US 2004/0022879 A1   Feb. 5, 2004

(51) Int. Cl.
*A01K 35/78*   (2006.01)
(52) U.S. Cl. .................................... 424/725
(58) Field of Classification Search ............... 424/725, 424/195.1
See application file for complete search history.

(56) References Cited

U.S. PATENT DOCUMENTS

| 4,576,956 | A | * | 3/1986 | Makisumi et al. ........... 514/380 |
| 4,778,798 | A |   | 10/1988 | Brasey |
| 5,089,636 | A | * | 2/1992 | Kwak et al. ................. 549/297 |
| 5,481,043 | A | * | 1/1996 | Wagner et al. ............... 568/309 |
| 5,952,373 | A |   | 9/1999 | Lanzendorfer et al. |
| 5,976,548 | A |   | 11/1999 | Hsia et al. |
| 6,492,429 | B1 | * | 12/2002 | Graus et al. ................. 514/688 |

FOREIGN PATENT DOCUMENTS

AU          702894          5/1997

OTHER PUBLICATIONS

Webb, D. MSM: Natural Cure for Pain? Prevention, Aug. 1999. vol. 51, Issue 8, p. 52, 2 pgs, accessed from ProQuest direct on the WWW, pp. 1-2.*

* cited by examiner

*Primary Examiner*—Patricia Leith
(74) *Attorney, Agent, or Firm*—Flynn, Thiel, Boutell & Tanis, P.C.

(57) ABSTRACT

A composition including (a) a Platelet Activating Factor (PAF) Inhibitor and (b) an antioxidant which interferes with the arachidonic acid cascade and also has antioxidant activity. The composition is useful for the treatment or the relief of inflammatory diseases, thrombosis, cardiac problems, and/or conditions caused by platelet induced blood clotting.

20 Claims, 3 Drawing Sheets

PREPARATION FOR THE RELIEF OF DISEASE

The present invention relates to preparations for the treatment or relief of diseases, especially inflammatory diseases, in humans and animals. In particular it relates to preparations for the treatment of inflammatory respiratory diseases such as asthma in humans, especially in children.

Asthma is a chronic disease of the airways characterized by recurrent airway obstruction. Known treatments of asthma include daily doses of pharmaceuticals such as inhaled corticosteroids, antihistamines and inhaled beta agonist bronchodilators such as Ventolin (RTM). The aim of such treatments is to manage or ameliorate the condition, that is to provide symptomatic relief of wheezing and/or breathlessness and/or coughing. Unfortunately, even with such treatments, asthma sufferers are prone to severe asthma attacks or crises which may be brought on or exacerbated by other illness such as colds or influenza, allergens (for example pollen, house dust etc.) or by exercise. Such crisis points may involve unremitting coughing and other respiratory distress, and may necessitate hospitalization and/or out-patient emergency care to administer repeated bronchodilation therapy, oxygen therapy, and high doses of oral glucocorticosteroids.

A major goal of asthma therapy is the prevention of crises which require emergency therapy and/or oral corticosteroid treatment. This is for two major reasons. First, it is the crises which are the major cause of the morbidity and mortality associated with asthma. Secondly, recurrent steroid use, especially at high doses of oral steroids, is associated with multiple adverse affects, which are well documented.

Inhalation therapy of asthma using an inhaler is the standard treatment for attacks other than severe acute attacks but has several disadvantages. It requires coordination of discharge of the inhaler with inhalation, which many people, especially children, find difficult. It also requires considerable respiratory effort which those suffering from asthma find difficult.

Beta 2 bronchodilators, e.g. salbutamol (Ventolin) and terbutaline (Bricanyl) are usually taken by inhalation but may be taken orally. When taken orally, these compounds have considerable adverse effects, such as inducing tremor and/or cardiovascular side effects (such adverse effects can also follow inhalation administration but are less likely). The side effects are particularly bad at high doses. Oral steroids, e.g., prednisolone and prednisone, which are used in acute asthma attacks, also have known (and considerable) side effects; these compounds are generally taken for a short period in order to alleviate the attack while avoiding those side effects.

Thus, known oral treatments for asthma either suffer from the severe and well known side effects associated with glucocorticosteroids, or have not proved very effective. There is, therefore, a considerable need for an effective oral treatment for asthma and other respiratory diseases.

According to the present invention, there is provided a composition including (a) a Platelet Activating Factor (PAF) Inhibitor and (b) an antioxidant which interferes with the arachidonic acid cascade. Preferably, the antioxidant (b) is an NADPH oxide inhibitor. Preferably, the antioxidant (b) increases glutathione synthesis. Antioxidant (b) is preferably a neutrophil oxidative burst antagonist.

Platelet-activating factor (PAF) is an ether-linked phospholipid (acetyl glycerol ether phosphocholine) produced by many different kinds of stimulated cells (e.g., basophils, neutrophils, monocytes, macrophages, endothelial cells) from phospholipids which are mobilized from cell membranes by phospholipase A2. It is 100-to-10,000 times more potent than histamine with respect to its vasoactive properties. As one of its smooth muscle effects, it is a strong bronchoconstrictor. It also stimulates other cells to increase their functional and metabolic activities, i.e., primes or activates them for more effective function. It is a potent platelet-aggregating agent and inducer of systemic anaphylactic symptoms.

PAF inhibitor should be taken to mean an agent which inhibits PAF by any mechanism.

Preferably the Platelet Activating Factor (PAF) Inhibitor (a) is a ginkgolide. Preferably the source of ginkgolide(s) is *ginkgo biloba*, or extract or component thereof.

Ginkgolides, for example, ginkgolide B, display potent (PAF) inhibiting activity. This may lead to reduction of bronchoconstriction, induction of airways hyperactivity and eosinophil response.

The structure of ginkgolide B (Molecular Formula: $C_{20}H_{24}O_{10}$) is shown below.

Gingkoilde B

The ginkgolides are bioactive terpenes isolated from the roots, bark and/or leaves of *Ginkgo biloba* L., *Ginkgoaceae*. Other suitable ginkgolides are those compounds which can be extracted from, for example, the roots, bark and/or leaves of *Ginkgo biloba* L., *Ginkgoaceae* by a polar organic solvent.

Arachidonic acid (AA) is the substrate from which eicosanoids, e.g., prostaglandins, leukotrienes, and numerous other mediators, are produced. Eicosanoids can collectively mediate almost every aspect of the inflammatory response. AA is produced from membrane phospholipids and fatty acids through the effects of various phospholipases. AA is not stored in cells, however, it is produced and metabolized into mediators very rapidly. The process by which eicosanoids is made (from AA) is termed the arachidonic acid AA cascade, and is well known. The main mediating enzymes in the AA cascade are of the cyclooxygenase class, enzymes principally inhibited by aspirin and other NSAIDS, as well as COX-2 inhibitors.

By "an antioxidant which interferes with arachidonic acid cascade" it is meant any antioxidant that affects any stage of the AA cascade (for example by inhibition of a mediating enzyme). The antioxidant may be said to have two modes of action: (i) an antioxidant action; and (ii) an action which affects the AA cascade.

Preferably, the antioxidant (b) is apocynin. This may be in isolated form (e.g. apocynin), a precursor, for example the dimmer, the Glucoside (for example androsin), glycone or in the form of acetovanillone), and/or apocynin in natural form (e.g., in the form of *picrorrhiza kurroa*). These forms are discussed in more detail below.

The compositions, preparations and methods according to the invention are useful as (or in the manufacture of) pharmaceutical preparations for the treatment of human patients, and/or as (or in the manufacture of) veterinary preparations for the treatment of non-human animals because they demonstrate activity as discussed below and shown in test data (see, for example, Example 13). The tests indicate that the composition(s) and/or preparation(s) are suitable for use in the treatment or amelioration or relief of inflammatory disease. Preferably, they are used for the treatment or amelioration or relief of inflammatory respiratory disease. "Inflammatory respiratory disease" includes respiratory diseases such as asthma, allergic airways disease and emphysema (e.g., hereditary emphysema), symptoms of allergy manifested in the respiratory system, exercise induced asthma and Chronic Obstructive Pulmonary Disease (COPD) (bronchitis). The preparation may also be used to treat inflammatory diseases such as inflammatory joint disease, arthritis and rheumatoid osteoarthritis, (atopic) dermatitis, leishmaniasis and/or inflammatory diseases of the gastrointestinal tract, such as ulcers (including stomach ulcers, gastric ulcer syndrome, ulcerative colitis, coeliac disease, Irritable Bowel syndrome, Irritable Bowel Disease and Crohn's disease. The preparations may also be used to prevent Platelet Induced blood clotting, and thus are suitable for use in the treatment, management and/or prevention of conditions caused by Platelet Induced blood clotting (for example, Coronary Artery Disease, Arterial Clotting, PAD (peripheral arterial disease and Stroke). The preparations and compositions may also be used in the treatment, management and/or prevention of thrombosis and cardiac related problems (for example ischemia and blood flow problems, arrhythmias induced by experimental myocardial ischemia, prevention or reduction of arteriolar spasms and problems caused by thrombus formation).

The compositions and preparations may be used to treat, manage, or prevent hayfever (allergic rhinitis). Preferred compositions for this use further comprise dimethyl sulfone.

The compositions may be used as (or in the manufacture of) veterinary preparations for the treatment of non-human animals, for example, dogs, pigs, equine species, poultry and reared game birds such as pheasants. They may be used to treat inflammatory diseases such as seasonal pruritic dermatitis, laminitis, eczematous dermatitis, COPD, lameness, azoturia, dermatitis, rain scald, osteoarthritis, hip dysplasia and leishamaniasis, equine gastroulcer syndrome, or the sequellae thereof., The combination of pharmaceutically significant amounts of active ingredients, antioxidant (b) (e.g., apocynin) and PAF Inhibitor (e.g. *ginkgo biloba*), may have a synergistic effect that leads to extremely efficacious treatment of diseases, for example, asthma. Treatment using preparations of the invention may lead to considerable benefits in general health, such as up to a 95% reduction in symptoms of asthma and other more general manifestations, such as increased wellness and happiness, color (indicative of improved oxygenation), and, in children, apparent increased growth and development. There may also be a significant reduction in the amount of crises and thus a decreased need for hospital or out-patient treatment.

"Treatment using preparations of the invention" should be taken to mean both administration of the preparation as a preventative or maintenance dose with the aim of prophylaxis (that is preventing or at least reducing the frequency of attacks and therefore maintaining a level of health, and/or preventing the development of a condition), and treatment at a (generally higher) "therapeutic level" to alleviate chronic attacks or crisis symptoms which, if untreated, may lead to hospitalization. Thus, the preparation may remove or reduce the need for treatments considered harmful such as corticosteroids, especially oral corticosteroid treatments. However, the preparations/compositions may be administered in combination with conventional asthma treatments (Ventolin, oxygen therapy, corticosteroids, breathing techniques, etc.) without ill effects, and may enable the dose of conventional treatment to be reduced (dose sparing).

Examples of compositions suitable for use as an antioxidant (b) are NADPH-oxidase inhibitors such as catechols and their metabolites and methylated catechols, for example, apocynin.

Preferably, the antioxidant (b) is apocynin which is the plant-phenol 4-hydroxy-3-methoxyacetophenone, and has the following formula:

Apocynin interferes with the arachidonic acid cascade, increases glutathione synthesis, and is a neutrophil oxidative burst antagonist. These effects may contribute to the increased therapeutic effects shown by preparations including apocynin.

The antioxidant (b) may also be an apocynin derivative or a phenone derivative. Some examples of suitable phenone derivatives are disclosed in U.S. Pat. No. 5,481,043.

NADPH-oxidase inhibitors (suitable for use as antioxidant (b)) may be found in plant substances and plant extracts. For example, apocynin is found in extracts of the plants *picrorrhiza kurroa, apocynum cannabinium, apocynum venatum* or *apocynum androsaemifolium*. The preparations of the invention may include an "isolated" NADPH-oxidase inhibitor (for example "isolated" apocynin). Isolated NADPH-oxidase inhibitor is an NADPH-oxidase inhibitor which has been synthesized, or NADPH-oxidase inhibitor which has been extracted from plants and purified. Apocynin (or other NADPH-oxidase inhibitors) may be present in preparations according to the invention as direct extracts from plants (i.e., as part of an unresolved mixture of compounds in the form of an unpurified plant or root extract). These will be referred to as NADPH-oxidase inhibitors (or apocynin) "in the natural form". For example, apocynin present in preparations according to the invention in the form of *picrorrhiza kurroa* will be referred to as "natural apocynin". Natural apocynin may include androsin and other iridoid glucosides, for example.

Preferably the composition includes antioxidant (b) which is an NADPH-oxidase inhibitor in a purified or synthetic form: "isolated" NADPH-oxidase inhibitor.

It is a still further preference that the antioxidant (b) which is an NADPH-oxidase inhibitor is present in both isolated form and a natural form.

As discussed above, the preferred antioxidant (b) is apocynin. If apocynin is used in the preparation in "isolated form", it is a further preference that the preparation also comprises a natural form of apocynin, for example, from an apocynin containing plant such as *picrorrhiza kurroa, apocynum cannabinium, apocynum venatum* or *apocynum androsaemifolium*, most preferably an extract from *picrorrhiza kurroa*. The use of the active entity in the natural form in combination with the "isolated" active entity may lead to a further synergistic effect between the isolated form (e.g., purified or synthetic apocynin) and the natural form (e.g., apocynin contained in *picrorrhiza kurroa*). The preferred *picrorrhiza kurroa* is a standardized form based on standardized iridoid glucoside fractions such as are well known. A preferred *picrorrhiza kurroa* in standardized form comprises standardized iridoid glucoside fractions collectively known as "Kutkin min 4%". Standardized iridoid glucoside fractions between Kutkin min 2% and Kutkin min 8% are also preferred. In the Examples below, the *picrorrhiza kurroa* in standardized form comprises standardized iridoid glucoside fractions collectively known as "Kutkin min 2%".

The composition may include antioxidant (b) which is an NADPH-oxidase inhibitor in natural form only, for example, picrorrhiza kurroa. However, if this is the case, it may be necessary to limit the amounts of *picrorrhiza kurroa* to prevent side effects (such as upset stomach which may occur due to other species in the *picrorrhiza kurroa*). However, it is noted that most human subjects can take up to 2,000 mg of *picrorrhiza kurroa* (Kutkin min 2%) per day without discomfort.

A preferred composition comprises:
a) *ginkgo biloba*; and
b) antioxidant, preferably NADPH-oxidase inhibitor, preferably apocynin;

wherein the ratio by weight of *ginkgo biloba*:antioxidant is between about 3:10 and about 3.4:1, preferably between about 0.5:1 and about 3:1, and more preferably between about 2.1:1 and 2.7:1.

In the ratio above, the weight of antioxidant refers to the weight in the isolated form (e.g., apocynin in the isolated form).

Thus, according to the invention, in another aspect there is provided a pharmaceutical preparation for the treatment or relief of inflammatory disease, thrombosis, cardiac problems and/or conditions caused by Platelet Induced blood clotting comprising (a) a Platelet Activating Factor (PAF) Inhibitor and (b) an antioxidant which interferes with the arachidonic acid cascade. Preferably, the antioxidant (b) is an NADPH oxide inhibitor. Preferably, the antioxidant (b) increases glutathione synthesis. Antioxidant (b) is preferably a neutrophil oxidative burst antagonist.

Preferably the Platelet Activating Factor (PAF) Inhibitor is *ginkgo biloba*. Preferably the antioxidant (b) is apocynin.

The apocynin may be in isolated form. Preferably, the preparation further comprises apocynin in the natural form. Preferably the preparation is a pharmaceutical preparation for the treatment of inflammatory diseases in humans. Preferably, the preparation is for the treatment of inflammatory respiratory diseases.

A preferred pharmaceutical preparation for inflammatory disease comprises:
a) *ginkgo biloba*; and
b) antioxidant, preferably NADPH-oxidase inhibitor, preferably apocynin;

wherein the ratio by weight of *ginkgo biloba*:antioxidant is between about 3:10 and about 60:1, preferably between about 6:1 and about 0.4:1, more preferably between about 2.4:1 and about 0.45:1, even more preferably between about 2.1:1 and about 1.4:1.

In the ratio above, the weight of antioxidant refers to the weight in the isolated form (e.g., apocynin in the isolated form).

The preparations and compositions in the preceding paragraphs assume the *ginkgo biloba* is in natural form. Preferably the *ginkgo biloba* is in concentrated standard form, for example, a concentrated extract which is equivalent to four times the concentration of *ginkgo biloba* in the natural form, such as *Ginkgo biloba* tablets sold by MediHerb of Australia (500 mg tablets containing *ginkgo biloba* concentrated extract equivalent to 2.0 g dry leaf *ginkgo biloba* standardized to *Ginkgo* flavone glycosides). Thus, a preferred preparation which includes *ginkgo biloba* in such a concentrated standard form comprises:
a) *ginkgo biloba* (in concentrated standard form);
b) an antioxidant, preferably NADPH-oxidase inhibitor, preferably apocynin;

wherein the ratio by weight *ginkgo biloba*:antioxidant is between about 30:1 and about 75:1000, preferably between about 3:1 and about 1:1, more preferably about 3:2.

It is noted that in preparations according to the invention, a level of antioxidant (b) (such as NADPH-oxidase inhibitor, for example, apocynin) higher than the minimum value specified above makes the preparation more suitable for a therapeutic treatment, while an amount of antioxidant (b) of around the minimum value noted above makes the preparation more suitable for a standard preventative measure treatment.

Preferably, the composition (or preparation) further comprises an agent which enhances lipid solubility of the preparation. This gives rise to between absorption and, hence, better bioavailability, especially by the oral route. Preferred agents which enhances lipid solubility are sources of pharmaceutically acceptable surfactants and/or fatty acids, for example, phosphatidycholine (lecithin).

Preferably, the compositions or preparations further comprise dimethyl sulfone. Such preparations are especially suitable for treating hayfever (allergic rhinitis).

The preparation may further comprise additional components such as pharmaceutically conventional carriers, diluents, flavourants, emulsifiers and stabilizers. Preferably the preparation further comprises one or more of the following:
i) an agent to enhance the immune system, for example, lactoferrin which has anti-viral, antibacterial and anti-oxidant effects;
ii) a natural source of vitamins or minerals such as bee pollen;
iii) a source, for example, a natural source, of vitamins, minerals and amino acids, for example, *chlorella;*
iv) a source of trace elements, for example, *fucus vesiculosus;* and/or
v) taste-masking agents, for example, yogurt, fruit juice, honey and syrup.

The compositions and preparations are suitable for oral administration. Thus, in another aspect, the present invention provides an orally bioavailable preparation for the treatment or relief of inflammatory disease, thrombosis, cardiac problems and/or conditions caused by Platelet Induced blood clotting comprising (a) a Platelet Activating Factor (PAF) Inhibitor and (b) antioxidant which interferes with the arachidonic acid. Preferably, the antioxidant (b) is an NADPH oxide inhibitor. Preferably, the antioxidant (b) increases glutathione synthesis. Antioxidant (b) is preferably a neutrophil oxidative burst antagonist.

Preferably, the Platelet Activating Factor (PAF) Inhibitor (a) is *ginkgo biloba*. Preferably, the antioxidant (b) is apocynin.

In a still further aspect, the present invention provides an orally bioavailable preparation for the treatment of inflammatory respiratory disease comprising *ginkgo biloba* and apocynin. The apocynin may be in isolated form (e.g., apocynin as the dimmer, glycone or in the form of acetovanillone) or in natural form (e.g., in the form of *picrorrhiza kurroa*). Preferably, the apocynin is present in natural and isolated forms.

Thus, the invention may provide an orally active antiasthmatic preparation. It will be appreciated that the preparations are suitable for other means of administration, for example, mucosal delivery routes (for example, rectal, nasal, vaginal) and also topical administration.

According to the present invention, there is also provided a method of treatment or relief of inflammatory disease, thrombosis, cardiac problems and/or conditions caused by Platelet Induced blood clotting in human or other animal subjects comprising the step(s) of administering to the subject (a) a Platelet Activating Factor (PAF) Inhibitor and (b) an antioxidant which interferes with the arachidonic acid cascade.

Preferably, the antioxidant (b) is an NADPH oxide inhibitor. Preferably, the antioxidant (b) increases glutathione synthesis. Antioxidant (b) is preferably a neutrophil oxidative burst antagonist. The present invention also provides a method comprising use of (a) a Platelet Activating Factor (PAF) Inhibitor and (b) an antioxidant which interferes with the arachidonic acid cascade in the manufacture of a medicament for the treatment of inflammatory disease in humans or other animals.

Preferably, the method is for the treatment (and/or amelioration or relief) of inflammatory respiratory diseases, for example, those discussed in the paragraphs above, for example, asthma, allergic airways disease and emphysema (for example, hereditary emphysema), hayfever, allergic rhinitis, symptoms of allergy manifested in the respiratory system, exercise induced asthma and Chronic Obstructive Pulmonary Disease (COPD) (bronchitis). The method may also be used to treat inflammatory diseases such as inflammatory joint disease, arthritis and rheumatoid osteoarthritis, and/or inflammatory diseases of the gastrointestinal tract, such as ulcerative colitis, coeliac disease, Irritable Bowel syndrome, Irritable Bowel Disease and Crohn's disease. The method may be used to prevent platelet induced blood clotting, thrombosis, cardiac problems and other conditions discussed above.

Preferably, the Platelet Activating Factor (PAF) Inhibitor is *ginkgo biloba*. Preferably, the preparation is administered to a human at a concentration, per daily dose, of *ginkgo biloba* (standardized to *ginkgo* flavone glycosides—24%) of 1 mg/kg body weight—25 mg/kg body weight.

Preferably, the antioxidant (b) is apocynin. Preferably, the preparation is administered to a human at a concentration, per daily dose, of apocynin of 60 µg/kg body weight—20 mg/kg body weight.

Preferably, the method further comprises the step of administering a natural form of antioxidant (b), as described above, for example *picrorrhiza kurroa*. Preferably, the preparation is administered at a concentration, per daily dose, of *picrorrhiza kurroa* of 1 mg/kg body weight—35 mg/kg body weight. This preferred daily dose of *picrorrhiza kurroa* is based on standardized iridoid glucoside fractions collectively known as "Kutkin min 4%".

The above ranges are a maintenance dose (for prophylactic treatment) for a human patient. For a loading dose (e.g., to begin treatment or treat an acute attack) the daily dose should be doubled for a period of 1–5, preferably 3 days.

There may be a cumulative effect which provides clinical benefits over a longer period of 10 to 30 days.

The daily dose may be provided as a single capsule, tablet or other solid or liquid form known to those skilled in the art, or may be provided in divided doses (for example, 1 to 3 doses) to make up the full daily dose. The doses of *ginkgo biloba* and antioxidant (b), for example, apocynin, may be provided together in the capsule, tablet, etc., or the two may be provided as separate capsules or tablets (a capsule containing dose or partial dose of *ginkgo biloba*, and a separate capsule containing the antioxidant (b), for example, apocynin) for sequential administration.

The following are preferred compositions/doses for the treatment of animals. The preferred Platelet Activating Factor (PAF) Inhibitor is *ginkgo biloba*. Preferably, the antioxidant (b) is apocynin. Preferably, the method further comprises the step of administering a natural form of antioxidant (b), as described above, for example, *picrorrhiza kurroa*.

For dogs, the preferred doses are a concentration, per daily dose, of *ginkgo biloba* (standardized to *ginkgo* flavone glycosides—24%) of 1 mg/kg body weight—7 mg/kg body weight; a concentration, per daily dose, of apocynin of 0.6 mg/kg body weight—35 mg/kg body weight. The dose may also comprise a daily dose of *picrorrhiza kurroa* of 3 mg/kg body weight—6.6 mg/kg body weight. The preferred daily dose of *picrorrhiza kurroa* is based on standardized iridoid glucoside fractions collectively known as "Kutkin min 4%".

For horses, the preferred doses are a concentration, per daily dose, of *ginkgo biloba* (standardized to *ginkgo* flavone glycosides—24%) of 4 mg/kg body weight—23 mg/kg body weight; a concentration, per daily dose, of apocynin of 0.2 mg/kg body weight—1.1 mg/kg body weight. The dose may also comprise a daily dose of *picrorrhiza kurroa* of 1 mg/kg body weight—5.6 mg/kg body weight. The preferred daily dose of *picrorrhiza kurroa* is based on standardized iridoid glucoside fractions collectively known as "Kutkin min 4%".

According to the present invention in a further aspect, there is provided a kit of parts for a preparation for treatment or prevention of inflammatory disease, thrombosis, cardiac problems and/or conditions caused by Platelet Induced blood clotting in human or other animal subject comprising at least one dose of (a) a Platelet Activating Factor (PAF) Inhibitor and (b) an antioxidant which interferes with the arachidonic acid cascade. Preferably the Platelet Activating Factor (PAF) Inhibitor is *ginkgo biloba*. Preferably the antioxidant (b) is apocynin.

It is envisaged that the kit of parts may be provided as, for example, a blister pack containing capsules containing doses or partial doses of, for example, *ginkgo biloba*, and separate capsules containing doses or partial doses of the antioxidant (b) (e.g., apocynin). The pack may be provided with instructions for sequential administration of the doses.

When administered either together or separately, the compounds (a) and (b) should be such as to maintain a suitable blood level of each of (a) and (b). When administered separately, the compounds (a) and (b) should be given within four hours of each other, preferably within two hours, and more preferably simultaneously.

Preferably, the inflammatory disease is inflammatory respiratory disease, for example, asthma. The disease may be allergenic in nature.

It is preferred that the preparation is administered orally, for example, in pill or capsule form, although it is possible to use other known conventional administration techniques.

The compositions (and preparations) of the invention may be used as a sole treatment. They may also be used alongside conventional medicines (e.g., anti-allergics such as steroids and antihistamines which have unwanted side affects); this may lead to a reduction in the dose of conventional medicine required and thus a reduction in likelihood/occurrence of the side effects. A reduction of side effects of a therapeutic agent (for example, the side effects of anti-allergic agents) during treatment of human or animal patients being treated is known as "dose sparing".

Thus, according to the invention in a still further aspect, there is provided a method of dose sparing a therapeutic agent comprising the step of administering to the patient a preparation comprising (a) a Platelet Activating Factor (PAF) Inhibitor and (b) an antioxidant which interferes with the arachidonic acid cascade. Preferably, the Platelet Activating Factor (PAF) Inhibitor is *ginkgo biloba*. Preferably, the antioxidant (b) is apocynin. The preparation may be administered at the same time as the therapeutic agent (for example, the anti-allergic agent) or at a different time, by the same administration route, or by a different administration route.

The examples and description relate (in places) to asthma but it will be understood that the preparations of the invention are suitable for treatment or amelioration or prevention of other diseases, especially other inflammatory diseases, as discussed above. These may be, for example, other respiratory inflammatory diseases such as emphysema. It will also be understood that, amongst other things, the preparations of the invention are suitable for treatment or diminution of the symptoms of allergic attacks or allergic reactions such as insect bites or stings. The preparations of the invention are suitable for treatment, amelioration or prevention of inflammatory gastrointestinal tract disorders. The preparations of the invention are suitable for treatment or prevention of inflammatory diseases, e.g., inflammatory respiratory disease in animals, for example, dogs and horses.

DETAILED DESCRIPTION OF THE INVENTION

Embodiments of the present invention will now be exemplified and illustrated with reference to the attached Figures, in which.

EXAMPLE PREPARATIONS

Example 1

The following reagents were mixed:

| | |
|---|---|
| apocynin | 100 mg |
| picrorrhiza kurroa | 200 mg |
| lactoferrin | 60 mg |
| ginkgo biloba** | 150 mg |
| bee pollen | 120 mg |
| chlorella pyrenoidosa | 250 mg |

-continued

| | |
|---|---|
| phophatidylcholine (lecithin) | 100 mg |
| fucus vesiculosus | 20 mg |

The lactoferrin, bee pollen, *chlorella pyrenoidosa*, phosphatidycholine (lecithin) and *fucus vesiculosus* serve as the vehicle.
**The ginkgo biloba used was a concentrated extract equivalent dry leaf (that is concentrated at a ratio 1:4) and standardizd to ginkgo flavone glyosides ~18%. Thus, for the same concentration, 600 mg of "natural" ginkgo biloba would be used.

The mixture was divided and prepared in a form suitable for dosing, for example, in capsule form for oral dose.

Example 1 A

The following compounds were mixed and used for adults and larger children:

| | |
|---|---|
| apocynin | 180 g |
| picrorrhiza kurroa | 360 g |
| gingko biloba** | 260 g |
| chlorella pyrenoidosa | 100 g |
| phosphatidyl choline (leicithin) | 100 g |

**gingko biloba: concentrated extract equivalent to dry leaf 1:4 standardised to gingko flavone glycosides ~24%.

425 mg (size 0 capsules) per 16 kg body weight: split approximately twice daily ⅖ doses in the a.m. and ⅗ doses in the p.m.

Example 1 B

The following compounds were mixed and used for smaller children:

| | |
|---|---|
| apocynin | 100 g |
| picrorrhiza kurroa | 200 g |
| ginkgo biloba** | 150 g |
| bee pollen | 100 g |
| chlorella pyrenoidosa | 280 g |
| phosphatidylcholine (lecithin) | 150 g |
| fucus vesiculosus | 20 g |

**gingko biloba: concentrated extract equivalent dry leaf 1:4 standardized to gingko flavone glycosides ~24%.

425 mg (size 0 capsules) per 8 kg body weight: split twice daily ⅖ doses in the a.m. and ⅗ doses in the p.m. For small children, the capsule may be opened and the contents mixed in fruit yogurt.

Example 2

Preventative Treatment of Childhood Asthma

The subject, now a 10 year old girl, had an initial attack of bronchial asthma at 4 years old. Since then, her condition has been serious enough to require on numerous occasions immediate hospitalization and/or out-patient emergency care. Following an asthma crisis manifested as prolonged unremitting coughing and respiratory distress over some three days, which necessitated oxygen therapy, repeated broncho dilation therapy and corticosteroids, the subject was given a daily regime of a preparation according to Example 1.

The dose used was 425 mg of the mixed composition of Example 1 per 8 kg body weight (daily dose: 2,125 mg in total) split twice daily with ⅖ of the doses in the morning and ⅗ in the afternoon. At the end of 15 days of treatment, the subject became 80–90% symptom free, with an overall improvement in general health, activity and general well being. The subject no longer needed a daily dose (either single or combination dose of corticosteroids, antihistamines and/or bronchodilators; doses which had been necessary for five years prior to treatment). No side effects or problems were observed or reported.

Exercise induced asthma still occurred. However, this occurred significantly less frequently and was very much more manageable, generally with minimum bronchodilator therapy. The need for such therapy was further reduced by breathing exercises.

A similar significant response has been observed in children between the ages of 18 months and 15 years, although it is noted that with small children the dose may be administered by breaking open the capsule and mixing the dose in a more palatable medium, such as fruit yogurt or honey.

There may not always be an immediate clinical benefit but over a period of between 10 to 20 days, a general increase in health occurs due to the cumulative benefits of stabilization and a return to homeostasis. As with all "preventative therapeutic approaches", there remains the problem of compliance. If the subject stops taking the preparation, a reoccurrence of the clinical problems may occur.

During development of the therapy of Example 2, the synergistic effect of *ginkgo biloba* and apocynin was noted.

Comparison Example 1

Prior to the mixture of Example 1, the subject had been treated with *ginkgo biloba* alone. There was some improvement of the subject's condition but other medication was still needed; the frequency of use of medication (Ventolin inhaler) was reduced during the *ginkgo biloba* therapy from daily to 2/3 times per week.

Comparison Example 2

As discussed above, the mixture of Example 1 gave a 90% improvement in symptoms with the first subject, and tests generally gave an improvement of 85–95%, i.e., the subject was symptom free 85–95% of the time. However, administration of a second mixture omitting the *ginkgo biloba* showed an improvement in symptoms reduced to only 60%. Further treatment with the Example 1 mixture for 15 days increased the improvement to the remarkable 90% symptom free level.

Example 3

Treatment of Childhood Asthma: Therapeutic Dose

Example 2 provides a preventative or maintenance dose with the aim of preventing or reducing the frequency of attacks and, therefore, maintaining a level of health. The preparation is also suitable for treatment of the subject at a "therapeutic level" to alleviate crisis symptoms (e.g., prolonged unremitting coughing) which, if untreated, may lead to hospitalization. For treatment at a therapeutic level, the daily dose is increased by 3–5 times. That is, the daily dose is raised to 1275–2125 mg/kg body weight. In general, after 3 days at the therapeutic level, the crisis symptoms will have been alleviated and the subject's dose may then be reduced to the maintenance dose of Example 2.

Example 4

Adult Treatment of Asthma

An adult male subject reported asthma problems which he had suffered for some 6 to 7 years, caused by an allergy to a cat. The subject was, prior to treatment according to the invention, prescribed preventil and vanceril. These inhalers have been used daily by the subject for the previous 6 years (two puffs of each inhaler twice or three times daily). Attempts to reduce the medication were problematic and uncomfortable, leading to symptoms such as sleeplessness and breathlessness.

After administration of the dose and preparation of Example 1 for one week, the subject reported feeling "terrific". The subject also reported being able to reduce the frequency of use of preventil and vanceril (reduced to a frequency of one puff a day) without asthmatic flare-up or other side effects.

Example 5

The subject was a 4 year old boy who had had asthma since the age of 2, with a history of chronic ongoing asthma on his father's side of the family. His asthma was easily provoked by respiratory tract infections, but less so by environmental allergens. On occasions acute episodes had required emergency hospitalization and emergency management. Previous treatments used salbutamol (Ventolin) and inhaled corticosteroids (e.g.: Pulmicort/budesonide) as needed. He was treated with Example 1B for four months. Clinical examinations during subsequent respiratory tract infections have shown no clinical signs/manifestations of asthma. Since the start of the treatment, there has been no need for salbutamol or inhaled corticosteroids to control asthma. Salbutamol has been given, on occasion, during coughing episodes that occur during the infections, but this was not to control asthma; it appears that the irritant effect from the Salbutamol 'mist inhalation' provokes a productive sputum cough which resolves the coughing.

Example 6

The subject was a 70 year old man who had long term chronic obstructive pulmonary disease (COPD) exacerbated by occasional asthma. He had a typical pronounced barrel chested appearance and chronic shortness of breath coupled with chronic productive coughing. Previous treatment was with salbutamol (Ventolin) and inhaled corticosteroids (e.g.: Pulmicort/budesonide) as needed. He was treated with the composition of Example 1A and clinical observations at three weeks after the initial treatment, and thereafter over a period of 3 months, showed a significant change in facial coloring (blue to red/pink), and minimal productive sputum coughing. The patient claims to be 'feeling' somewhat improved and insists on continuing the treatment with the composition of Example 1A. There has been continued clinical improvement with minimum respiratory discomfort.

In addition to the chronic obstructive pulmonary disease, the patient suffers from rheumatoid arthritis and since taking the composition of Example 1A has observed a significant improvement of this condition. He is now able to undertake tasks and journeys on foot that have not been possible for some years.

Example 7

The subject was a 13 year old boy who had suffered from asthma since the age of 5 with a history of chronic ongoing asthma on his father's side of the family. Attacks were easily provoked by respiratory tract infections and by environmental allergens. On one occasion, an acute ongoing episode necessitated emergency hospitalization for 5 days. He was treated with salbutamol (Ventolin) and inhaled corticosteroids (e.g.: Pulmicort/budesonide) as needed. He was treated with the composition of Example 1B for 6 months starting after his hospitalization. After 14 days treatment, he showed no further clinical signs of asthma and his asymptomatic state continued for the 6 month period during which he took the composition. After ceasing to take the composition, there was a period of some four weeks before wheezing/asthma resumed.

Example 8

The subject was an 8 year old boy having asthma which was provoked by intense sport/exercise activity. He was treated with salbutamol (Ventolin) and inhaled corticosteroids (e.g.: Pulmicort/budesonide) as needed. After a period of hospitalization, he was given the composition of Example 1B. After 10 days of treatment, he displayed no clinical signs of asthma during sporting activities.

Example 9

The subject was a 40 year old woman who had suffered from asthma since childhood and was allergic to pollen and animals. Previous treatments included salbutamol (Ventolin) and inhaled corticosteroids (e.g.: Pulmicort/budesonide). After 28 days of taking the composition of Example 1, all daily inhaled corticosteroids were ceased (such medication having been taken daily for many years) and the patient reported a complete resolution of her asthma.

Example 10

The subject was a 40 year old man who had had asthma symptoms since childhood and who was allergic to animals (cats and horses). His allergies were exacerbated during summer months indicating a possible additional allergy to mixed pollens. He had been treated with Proventil and Vanceril over 6 years (two puffs of each 2 or 3 times per day). After 7 days treatment with the composition of Example 1, his asthma symptoms had resolved with minimum 'to be on the safe side' use of Proventil and Vanceril (1 per day of each). After a further two weeks treatment with the composition, he ceased taking the Proventil and Vanceril without return of asthma symptoms.

Example 11

The patient was a long term chronic asthma sufferer who was taking multiple medications (corticosteroids and bronchodilators). After taking the composition of Example 1A for about 10 days, he reported that his chest congestion was clearing and that he was breathing more confidently. He indicated that he no longer "hesitate(s) to run upstairs".

Example 12

Two children from the same family, both having long term histories of chronic respiratory disease with asthma-like symptoms and who did not obtain much benefit from using routine corticosteroids/bronchodilators, have, subsequent to taking the composition of Example 1B, been free of bronchial complications The girl, aged 8, has been taking 1 capsule in the morning and 2 capsules in the evening, and the boy, aged 6, has been taking one capsule in each of the morning and evening. Each child has also taken one capsule of dimethyl sulphone per day.

Example 13

In Vitro Studies

Extract Preparation

Extracts of components were prepared by stirring macerated samples overnight in methanol. The mixtures were centrifuged, the supernatants drawn off and dried to remove all traces of the extracting solvent. Resulting solids were re-suspended in normal saline (0.9% w/v NaCl) at saturated concentrations.

| Extract No. | Ingredient | Solvent |
| --- | --- | --- |
| 2 | Apocynin | Methanol |
| 5 | *Picrorrhiza kurroa* | Methanol |
| 8 | Ginko biloba | Methanol |

Method

Extracts 2, 5 and 8 were reconstituted in 0.9% saline at saturated concentrations.

Citrated whole blood, from healthy volunteers, was spun at 900 rpm for 20 minutes to obtain platelet rich plasma (PRP). Born aggregometry was then carried out within 1 hour of blood being taken. Extracts 2, 5, and 8 were added to 450 μl PRP either singly (6 μl), or in combination with one other extract (3 μl each), or all the extracts in combination (2 μl each). PRP was then stimulated with ADP (Sigma) $4 \times 10^{-6}$ M. 6 μl of saline was added to PRP for the control. Aggregation was measured in a PAP4C aggregometer (Bio-Data Corp. Horsham USA) over 10 minutes.

The dose of agonist was chosen to give slightly suboptimal aggregation thus showing the maximum effect of any inhibition. Doses of extracts were chosen to show the effect on platelets when used alone and any added and/or synergistic effect of using combinations. All data is recorded as the maximum aggregation.

Results

Figure 2:
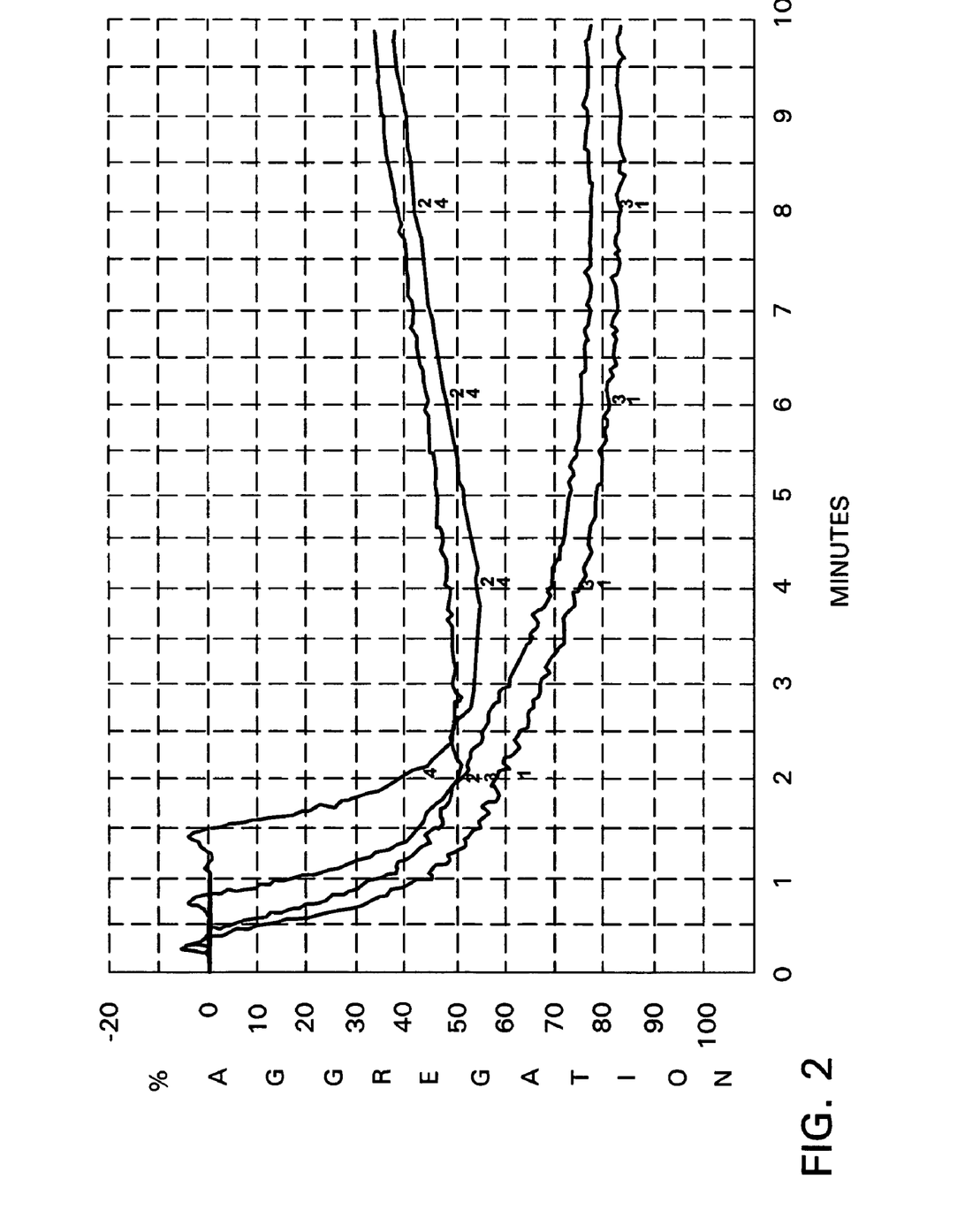
FIG. 2 shows the platelet aggregation response to ADP $4 \times 10^{-6}$ M in samples treated with 1) control; 2) 6 μl extract 2; 3) 6 μl extract 5; and 4) 6 μl extract 8 (Example 13)
Figure 3:
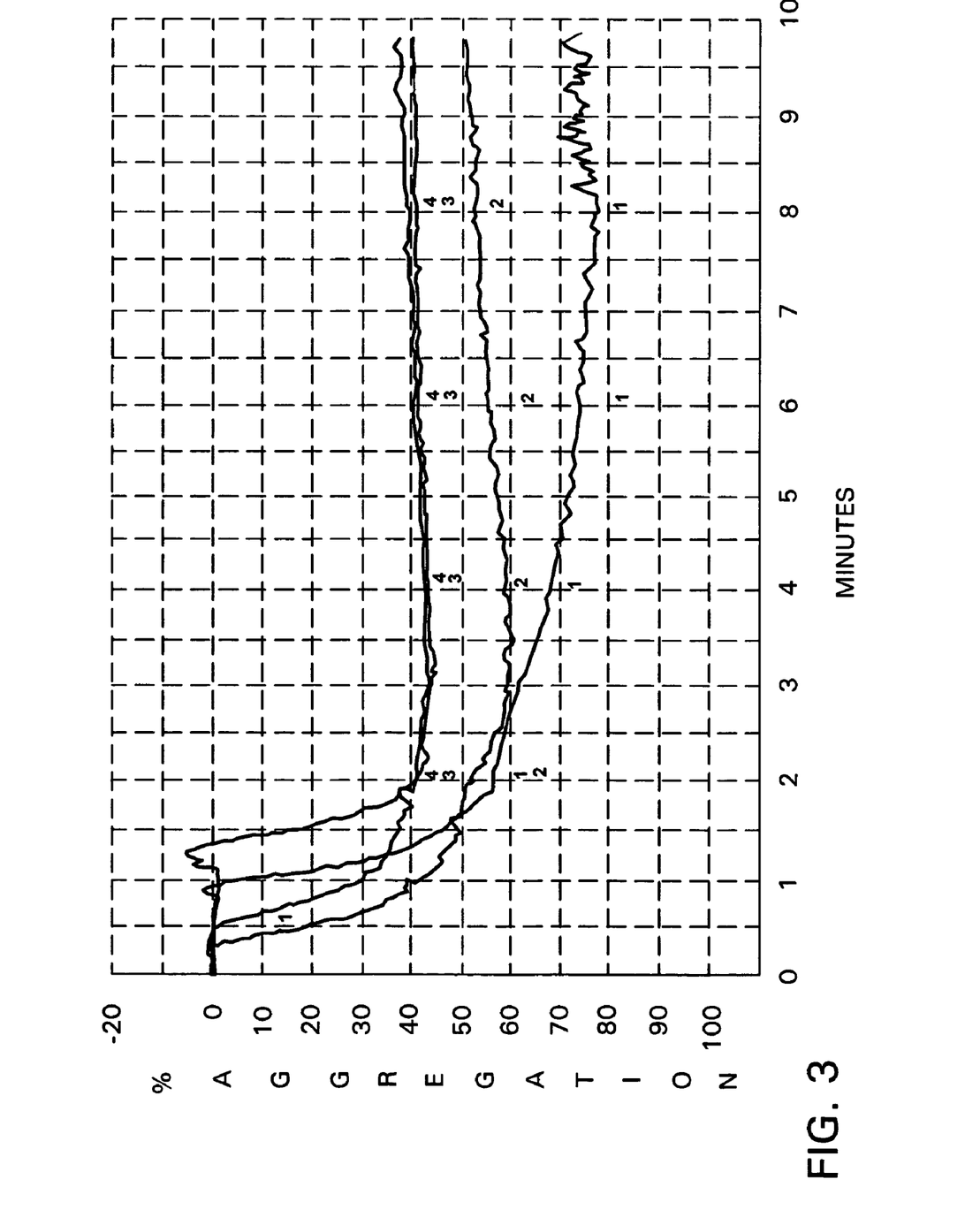
FIG. 3 shows the platelet aggregation response to ADP $4 \times 10^{-6}$ M in samples treated with 1) 3 μl extract 2 and 3 μl extract 5; 2) 3 μl extract 2 and 3 μl extract 8; 3) 3 μl extract 5 and 3 μl extract 8; and 4) 2 μl extract 2 and 2 μl extract 5 and 2 μl extract 8 (Example 13).

The results are shown in the following table ("Table Example 13") and FIGS. 1 to 3.

Figure 1:
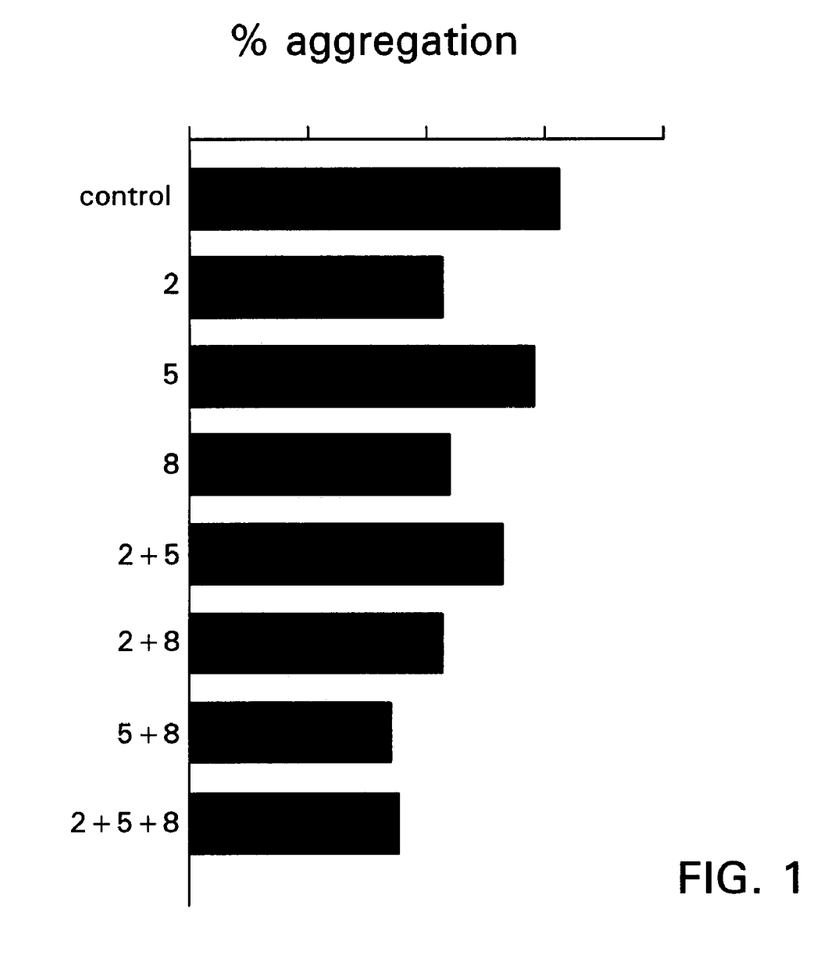
FIG. 1 shows the effect of Extracts 2, 5 and 8 alone or in combination on maximum platelet aggregation in response to ADP $4 \times 10^{-6}$ M (Example 13)

In the control treatment ADP $4 \times 10^{-6}$ M produce aggregation of 78.5% (Table 1 and FIG. 1).

| | |
| --- | --- |
| Extract 2 | (FIG. 1 + 2) aggregation in response to ADP reduced by 32% compared with the control. |
| Extract 5 | (FIG. 1 + 2) aggregation was reduced by 6%. |
| Extract 8 | (FIG. 1 + 2) aggregation reduced by 29%. |
| Extracts 2 + 5 | (FIG. 1 + 3) reduced ADP induced aggregation by 15%. |
| Extracts 2 + 8 | (FIG. 1 + 3) aggregation in response to ADP reduced by 31%. |
| Extracts 5 + 8 | (FIG. 1 + 3) reduced the response to ADP by 45%. |
| Extracts 2 + 5 + 8 | (FIG. 1 + 3) aggregation response to ADP reduced by 43%. |

Discussion

Extracts 2, 5 and 8 all reduced platelet aggregation in response to ADP. The combination of extracts 2+5 and 2+8 also caused a reduction in the ADP-induced aggregation. The combination of extracts 5+8 added to platelets reduced aggregation in response to ADP by 45% and the combination of extracts 2+5+8 reduced the response by 35%; both of these were greater than could be predicted by the additive effect of the extracts alone. Thus, in these combinations {(5+8: *Picrorrhiza* and *Ginkgo biloba*) and (2+5+8: Apocynin and *Picrorrhiza* and *Ginkgo biloba*)} the inhibition caused by the extracts works in a manner that is at least greater than the predicted additive effect.

Leukotriene receptor antagonists are currently used and approved in the treatment of asthma. These compounds affect the signal transmission between platelets and immune cells. The components of the pathways associated with these receptors, e.g., arachidonic acid metabolism and PAF stimulation, all appear to be inhibited by the extracts of the apocynin, *Picrorrhiza kurroa* and *Ginkgo biloba* mixture.

The fact that the extracts of each component affect the activation of platelets and PMN (data not shown) differentially indicates that the extracts affect distinct elements of a number of different activation pathways. They demonstrate a higher effect on PMN than platelets which appears to support their primary action as an anti-inflammatory mixture in asthma.

The effects of the extracts on platelet aggregation show a marked inhibition of ADP-induced aggregation. ADP-induced aggregation is critically dependent on cyclooxygenase enzyme activity, an enzyme class blocked by aspirin and used extensively in blood clot prevention. These results provide strong support for the potential application of the mixture in reducing thrombosis and cardiac related problems (for example ischemia and blood flow problems, arrhythmias induced by experimental myocardial ischemia, prevention or reduction of arteriolar spasm and problems caused by thrombus formation).

The fact that there are significant gastrointestinal problems seen in the use of aspirin offers the mixture as a potential replacement for aspirin therapy. Furthermore, it has been well documented that aspirin can induce asthma. The compositions of the invention, as well as being useful in treatment of asthma, may be used instead of aspirin (or NSAIDs of the aspirin type) in treating conditions such as blood clotting in patients prone to asthma or similar conditions.

Table Example 13: Raw data showing the % aggregation in response to ADP in the presence of extracts 2, 5 and 8 alone or in combination.

| Extract | ADP $4 \times 10^{-6}$ M % Aggregation |
| --- | --- |
| control | 78.5 |
| 2-6 µl | 53.5 |
| 5-6 µl | 73.5 |
| 8-6 µl | 55.5 |
| 2-3 µl + 5-3 µl | 67 |
| 2-3 µl + 8-3 µl | 54 |
| 8-3 µl + 5-3 µl | 43 |
| 2-2 µl + 5-2 µl + 8-2 µl | 44.75 |

Veterinary Examples

Example 14 (Dogs)

Dosage apocynin: 10 mg—50 mg/15 kg body weight per day

*ginkgo biloba:* 20 mg—100 mg/15 kg body weight per day

*picrorrhiza kurroa:* 50 mg—100 mg/15 kg body weight per day phosphatidyl choline: 100 mg—200 mg/15 kg body weight per day.

The regime involves a loading dose (the high figures: apocynin 50 mg/15 kg body weight per day; *ginkgo biloba* 100 mg/15 kg body weight per day; *picrorrhiza kurroa:* 100 mg/15 kg body weight per day; and phosphatidyl choline: 200 mg/15 kg body weight per day) and a maintenance dose (the low figures: apocynin 10 mg/15 kg body weight per day; *ginkgo biloba* 20 mg/15 kg body weight per day; *picrorrhiza kurroa:* 50 mg/15 kg body weight per day; and phosphatidyl choline: 100 mg/15 kg body weight per day).

The loading dose is from three to ten days according to individual perceived clinical need. After the loading dose, the maintenance dose follows for a minimum (normally) of 30 days continuing as needed. The doses are scaled according to individual size/body weight.

The composition may be used to treat osteo-arthritic problems, hip-dysplasia and the mature (older/stiffer) dog. In acute cases, although non-steroidal anti-inflammatories (NSAIDs) are required, the NSAID dose can be routinely reduced to ⅛ the recommended/advised anti-inflammatory dose to achieve the same clinical pain relief when supplemented additionally with the compositions embodying the invention.

Example 14A

A Viszla (now 8 years old) with obliterative osteoarthritis (O/A) of both hind knee joints and O/A of left elbow joint. Originally (at age 2) was unable to bear weight on its hind limbs and now is clinically sound/well following treatment with the composition (much improved without need of NSAIDs or other anti-inflammatory medications).

Example 14B

A mixed-race dog with O/A from age of eight. Now clinically sound/well following treatment with the composition (much improved without need of NSAIDs or other anti-inflammatory medications).

Example 14C

A Doberman with Hip Dysplasia. Sound (much improved without need of NSAIDs or other anti-inflammatory medications) when taking the formulations of the invention. Unsound and unable to jump when not taking the formulations.

Example 14D

Labradors (several) with arthritis: sound when on formulations (much improved without need of NSAIDs or other anti-inflammatory medications) of the invention—previously unsound.

Example 14E

Treatment of Leishmaniasis (Canine)

This is a life-threatening problem that plagues the Mediterranean countries. It is, at best, debilitating and requires ongoing supportive medication with a poor prognosis. A Great Dane in a skeletal condition with multiple lymphadenopathies, pustular oozing lesions all over the body and 80% hair loss was presented after all conventional treatment regimes had failed. This condition is typical of the terminal phase of this disease. After 10 weeks of treatment with the formulations of the invention (Example 14), it was not possible to distinguish between this dog and normal healthy other members of his race, i.e., he was clinically normal.

Example 15 (Horses)

Dosage Horses (450 kg body weight).

apocynin: 100 mg—500 mg per day

*ginkgo biloba:* 2,000 mg—10,000 mg per day

*picrorrhiza kurroa:* 500 mg—2,500 mg per day phosphatidyl choline: 2,000 mg—10,000 mg per day The regime involves a loading dose (the high figures: apocynin 100 mg per day; *ginkgo biloba* 2000 mg per day; *picrorrhiza kurroa:* 500 mg per day; and phosphatidyl choline: 2000 mg per day) and a maintenance dose (the low figures: apocynin 500 mg per day; *ginkgo biloba* 10000 mg per day; *picrorrhiza kurroa:* 2500 mg per day; and phosphatidyl choline: 10000 mg per day).

The loading dose is from three to ten days according to individual perceived clinical need. After the loading dose, the maintenance dose follows for a minimum (normally) of 30 days continuing as needed. The doses are scaled according to individual size/body weight. The dose was added as a powder in the animals' feed.

The compositions used in the following Examples are:

JMJ (Apocynin Mixture)

400 kg of JMJ mix comprising Apocynin (acetovanillone) 0.188 kg and 9.2 kg *Picrorrhiza kurroa* root.

FRS (*ginkgo biloba* Mix)

103 kg of FRS includes 5 kg *ginkgo biloba.*

D-Tox

Includes 1 g *ginkgo biloba* per 15.05 g D-Tox.

JMJ, FRA and D-Tox are available from Nutrilabs of Penrhos, Raglan, Monmouthshire. They are used to make the following Example compositions according to the invention, which were used in Examples A to AA below. The following gives a daily dose for a 450 kg horse. With any of the following Example Compositions during ANY acute phase, a loading dose of 3 times the daily dose may be used to assist a rapid return to 'well being'.

Example PR

| dimethyl sulphone (MSM) | 2 mg |
|---|---|
| FRS | 10 mg |
| JMJ | 10 g |
| apocynin | 75 mg |
| ferulic acid | 100 mg |
| picrorrhiza kurroa | 100 mg |
| pancreas extract | 100 mg |

Example MG

Same as the EXAMPLE PR but includes a medicated shampoo and an MSM/Zinc-based cream for local application.

Example LA

| Dimethyl sulphone (MSM) | 2 g |
|---|---|
| FRS | 15 g |
| JMJ | 10 g |
| Apocynin | 200 mg |
| picrorrhiza kurroa | 250 mg |
| Chitin/Chitosan | 1 g |
| Salvia militorrhiza | 2 g |
| Thrive | 6 g |

The above gives a daily dose for a 450 kg horse.

Example RE

| dimethyl sulphone (MSM) | 3 g |
|---|---|
| FRS | 10 g |
| JMJ | 10 g |
| apocynin | 200 mg |
| picrorrhiza kurroa | 250 mg |

Example SU

| MSM | 2 g |
|---|---|
| FRS | 10 g |
| JMJ | 15 g |
| glucosamine | 500 mg |
| apocynin | 200 mg |
| chitin | 2 g |

Example D-Ty

| Viburnum opulus (bark) | 2 g |
|---|---|
| FRS Mix | 10 g |
| JMJ | 10 g |
| ferulic acid | 200 mg |
| cimicifuga racemosa | 1 g |
| Bynatone (11)# | 5 g |

Example PF

| Dimethyl sulphone (MSM) | 2 g |
|---|---|
| FRS | 15 g |
| JMJ | 10 g |
| Apocynin | 200 mg |
| picrorrhiza kurroa | 250 mg |
| Chitin/Chitosan | 1 g |
| Salvia militorrhiza | 2 g |
| Thrive (RTM) | 6 g |

Example DE

| | |
|---|---|
| dimethyl sulphone (MSM) | 2 g |
| equisetum arvense | 2 g |
| FRS | 10 g |
| JMJ | 15 g |
| urtica dioica | 2 g |
| angelica sinensis | 1 g |
| liver extract | 100 mg |
| salvia miltiorrhiza | 1 g |
| rehmannia glutinosa | 1 g |

The following compositions and methods are within the scope of the invention.

A. The horse is a 13 year old Welsh Section B mare that had suffered from Seasonal Pruritic Dermatitis since she was two years old. If left untreated, she would rub herself raw. Veterinary advice was sought and benzyl benzoate and stabling were advised. EXAMPLE PR was tried and an improvement was seen within three weeks. The mare now only rubs on very hot days and benzyl benzoate is only used on a very limited basis. The mare is now shown to be at a very high level of health.

B. The horse is a three-year-old Welsh Cob. Seasonal Pruritic Dermatitis was seen; veterinary advice was sought and benzyl benzoate was prescribed. EXAMPLE PR was tried and after five days the horse was doing very well and continues on a low maintenance level of EXAMPLE PR. The animal has been turned out over the summer for the first time in two years, with the only other product used being a fly repellent.

C. The horse is a 16.2 h.h, 14 year old mare that has suffered with Seasonal Pruritic Dermatitis on her stomach only during summer months since four years of age. She was also aggressive when that area was touched, e.g.: when the leg was applied. Veterinary advice was sought and many different approaches were tried but none worked. EXAMPLE PR was tried as a last resort and an improvement was seen within one tub. The mare now only rubs her stomach occasionally and seems much more content. She is easier and happier to ride.

D. The horse, aged 22, had suffered from Seasonal Pruritic Dermatitis for many years. Veterinary advice was sought and stabling, benzyl benzoate, garlic and antihistamine injections were advised. On advice, EXAMPLE PR was tried. An improvement was seen within one month and hair regrowth was seen within six weeks, while antihistamine treatments were no longer needed. The horse still rubs occasionally but has a main where previously it was bare, and the tail is no longer rubbed.

E. Housed at the same stable as horse D above, and aged 5, had suffered from Seasonal Pruritic Dermatitis for many years. EXAMPLE PR was tried. An improvement was seen within one month and hair regrowth was seen within six weeks. Antihistamines are no longer needed.

F. The horse had suffered from bad Eczematous Dermatitis and filled legs when stabled every year for the past six years. Veterinary advice was sought and a variety of treatments were tried. The results varied from improving the symptoms (Peridine shampoo) to worsening the condition (liquid paraffin). On advice, EXAMPLE MG was tried and an improvement was seen within one week. There was an 80% improvement in the filled legs, and no Eczematous Dermatitis occurred at all, all winter.

G. The horse is a 13.2 h.h 10 year old New Forest mare that had suffered from laminitis for four years. Veterinary advice had been sought. X-rays confirmed the condition and heartbar shoes, increased roughage in the diet, and restricted grazing were advised with only limited results. EXAMPLE L was used and an improvement was seen within two weeks. The pony is now fit and well and laminitis is not seem with EXAMPLE L being used as part of an overall management approach.

H. The horse is a 13.2 h.h, 12 year old mare who had previously suffered from laminitis when in foal. She was overweight when put in foal again and the laminitis recurred. Following unsuccessful treatments, it was decided to try EXAMPLE L; an improvement was seen within two days of commencement of treatment. Within six weeks, there was no sign of laminitis in the hoof.

I. The horse is a 14 year old Arabian mare which suffered with chronic COPD for many years. Veterinary advice was sought and Ventipulmin and steroids were tried. The mare deteriorated to the point where she couldn't even walk to her field. EXAMPLE RE was tried and an improvement was seen within one day. The horse is now a happy, fit animal.

J. EXAMPLE SU treatment of a hock deformity in a mare (which had caused lameness and impaired action) gave an "incredible difference" in action and soundness. Following a dressage competition, localized swelling, heat and intermittent lameness were seen in the near fore. Veterinary advice was sought. A mild strain to the check ligament was diagnosed; the horse was given a cortisone injection into the leg and box rest with controlled exercise was advised. As the mare was already on EXAMPLE SU, it was suggested that she try D-Tox as well (i.e., treatment continued with the effective concentration of *ginkgo biloba* increased). Three days after starting the D-Tox course, the swelling and heat had both noticeably reduced. Eleven days after starting, the leg had gone right down and all the heat had gone from it. The mare was still on box rest but was being led out to grave for up to 1½ hours daily. Overall the mare received a month's course of D-Tox. Two days after finishing the D-Tox, a flare-up of slight swelling and heat was seen again; however, this disappeared over the following two days with careful management. The mare continued on EXAMPLE SU throughout the whole treatment.

Thus, EXAMPLE SU plus D-Tox is within the scope of the invention; increase of concentration of *ginkgo biloba* may be used to manage chronic symptoms.

K. Following a number of traumas (a bad fall on the road and severe attack of colic), this horse developed COPD (chronic obstructive pulmonary disease) and a mite allergy at about the same time. The development of the problems also coincided with losing summer grazing and having to rely on 1 acre of poor grazing. The neighbor to the field continually has a dung heap burning (365 days a year), the prevailing wind is over the field and the owner considers that this must contribute to the respiratory condition. The COPD made it impossible to continue in competition and exercise. Horse K also suffered from an allergic reaction to mites in his fetlocks and heels which caused weeping, bleeding, pus and scabs. This is contributing to his reluctance to work. Ventipulmin (clenbuterol) and Dermobion (nitrofuazone, prednisolone, neomycin, chlorophyll, cod-liver oil) were prescribed by the attending veterinary surgeon. Ventipulmin had no effect. Dermobion only worked in the short term. The owner reported that EXAMPLE RE had a "more lasting beneficial effect". D-Tox was added and the owner reported a further improvement within three weeks, with full cure of the cough. Slight respiratory sounds are still heard during fast work, but prior to treatment he was previously unable to do fast work at all; these sounds may be due to permanent lung damage as this is a long standing condition (~5 years). Horse K can now go for two-hour hacks without any problem.

L. Having had the mare L for 15 years, the owner had no previous problems with either weight or laminitis. The vet diagnosed laminitis and prescribed Finadyne injections, followed by powder, remedial shoeing and Bute. A blood test revealed a hormonal imbalance. The mare had been on Bute for two months but reacted to it, with ulcers around the mouth and sores on the muzzle. The owner was recommended to try D-Tox and EXAMPLE LA. An improvement was seen within a week. The horse is now 95% sound.

M. Despite a careful management regime, the horse suffered from an acute onset of very severe laminitis; he could barely move. Veterinary advice was sought and Percutol ointment was tried on all eight digital pulses, along with four sachets of Bute a day, and box rest for six weeks. No great improvement was seen and the horse was given just 24 hours, by the vet, to show an improvement before being put down. The owner was advised to try D-Tox and EXAMPLE LA. Within twenty-four hours of starting the D-Tox, the horse had been reprieved from being put down, and within four days he was moving reasonably freely. He has no built up to three hours grass per day and continues to improve. On one day, a slight pulse was felt, and the horse was kept in with restricted diet and increased D-Tox (i.e., increased *ginkgo biloba*) and was fine again within twenty-four hours.

N. The horse is a twelve-year-old Trakehner x Arab mare who has suffered from occasional intermittent bouts of azoturia over the last six years. There seemed no particular reason for the attacks, and they usually occurred just after exercising. Veterinary advice was sought and vitamin E and selenium were suggested; this had no effect. The mare initially started on D-Tox which she was on for eight months before changing to EXAMPLE D-Ty. No incidence of typing up has been seen since the D-Ty was first introduced. The horse is on one scoop (11 g) of D-Ty together with salt and a broad based vitamin and mineral provider.

O. The horse is a twenty five year old Anglo Arab who has suffered with Eczematous Dermatitis continually for the past five years. Veterinary advice was sought and white lead lotion was advised. The owner decided to try EXAMPLE MG and NAF Teatree Oil Shampoo. Within three weeks, the swelling had reduced, the scabs were softening and falling off, and the skin started to heal very quickly. Within one month, the condition had healed completely for the first time in five years.

P. The horse is a 14.2 h.h. 12 year old cob that has suffered from Seasonal Pruritic Dermatitis (Sweet Itch) for a considerable time. Veterinary advice had been sought and "various lotions and potions" had been prescribed; none had had any significant effect. The owner decided to try EXAMPLE PR and saw an improvement within two weeks. There is still a little scratching, but not as severe. There is no inflammation or bald patches and he isn't forever against a tree or fence. The owner stopped using it for one week and noticed a reversal immediately.

Q. The horse is a 30 year old 13 h.h pony that began to itch. He would rub for up to 30 minutes at a time, chew himself until bleeding and developed bald weepy patches. The flanks, chest, rump and shoulders were affected, but not the mane or tail, and it continued throughout the winter so Seasonal Pruritic Dermatitis was ruled out. Veterinary advice was sought. Skin scrapings were taken, and nothing found. An "unspecified allergy" was diagnosed and medicated shampoo and steroids prescribed. The horse's owner was keen to avoid steroids and EXAMPLE PR was used. An improvement was seen in two days, and the owner was completely happy with the results within two weeks.

S. The horse is a 5 year old 15.2 h.h gelding who had suffered from Seasonal Pruritic Dermatitis since he was two and a half. The owner had tried several different products but none had worked and the horse's face, mane and tail were rubbed raw. EXAMPLE PR gave an improvement within a few weeks. Seasonal Pruritic Dermatitis is now well controlled when the animal is fed from April to late September.

T. The horse is a 16 h.h 12 year old Anglo Arab who suffered from Seasonal Pruritic Dermatitis and raised insect bites, first seen in the summer of 1999. EXAMPLE PR gave an improvement within four weeks of commencement, and the owner was completely happy with the results within six weeks. Any obvious insect bites now quickly disappear.

U. The horse is a 19 year old 12 h.h. Welsh Section A gelding. Seasonal Pruritic Dermatitis has developed since the age of 12, although mildly at first he now rubs mane, tail, rump and neck until raw. EXAMPLE PR gave a 90% improvement. The owner thinks that it has been even more successful when used as a preventative. With careful management, the horse now has a superb coat.

V. The horse is a 14 year old Irish Sport Horse who had always suffered from Eczematous Dermatitis, seen particularly as scabs on his fetlocks and swelling in his white legs. The owner tried EXAMPLE DE and noticed an immediate reduction in the swelling. Fuderex Cream was also used topically once the scabs had been removed; it was observed that the scabs did not reappear. The owner continued to use EXAMPLE DE and Fuderex Cream as a preventative measure throughout the risk period, and the horse remained well and unaffected.

W. The horse is an 11 year old Clysdale gelding who suffered with Eczematous Dermatitis every year. Veterinary advice had been sought and various injections, antibiotics, washes and creams were tried with little or no success. EXAMPLE DE gave an improvement within two weeks, despite the challenge being particularly great as the horse has unclipped, traditional, heavy horse feathers.

X. The animal is a 10 hh 10 year old donkey that had suffered with rain scald annually. Veterinary advice was sought and treating topically with Hibiscrub was prescribed. A course of antibiotics was used when the problem worsened. The owner was advised to try EXAMPLE DE to prevent the problem from reoccurring. It was obvious that the challenge was still present as slight scabbiness was seen in the early stages, but not as bad as previous years and it quickly cleared completely.

Y. The horse is a ten-year-old miniature Shetland who first suffered from a bout of laminitis in 1997. He remained clear of further attack until attending a show in May 1998 where he managed to graze on some rich grass. From that time onwards, the horse's owner described him as always being "just on the edge." Veterinary advice was sought from an equine specialist who took X-rays and said that the damage was not too great. Electrolytes were prescribed, however they had no effect and no improvement was seen. Treatment with EXAMPLE PF was so effective that the owner was "amazed by the improvement". Within one month of starting on EXAMPLE PF, the horse was better than he had been for a long time, even giving Bucking Bronco displays for the first time in years just for fun!

Z. The horse is a twenty-year-old pony that suffered his first attack of laminitis in June 2000. Veterinary advice was sought and he was given anti-inflammatory and pain killing injections, paste and a month's course of powder. An improvement was seen with EXAMPLE PF and the owner declared herself completely satisfied with the product's performance within one month. The horse is now well and walks out soundly, neither the foot nor sole are sore.

AA. The horse is a 3 year old Shetland gelding that suffers very badly with skin problems. In addition to Seasonal Pruritic Dermatitis during the spring and summer, he also suffers with hives, scabs, sores and poor coat condition year round. Veterinary advice was sought and dermatitis diagnosed. Dermobion and insecticidal shampoos were prescribed but no improvement was seen. The owner had also tried many of the other shampoos, washes, creams and supplements available but not had any effect. An improvement was seen within three weeks of starting EXAMPLE PR. The horse now has a clean coat, a 15 cm long mane and a whole tail. The coat is shiny, and the mane silkier. The horse is no longer scratching and his temperament has also improved, presumably due to him no longer being irritated.

Example 16

Example RE Plus

For treatment of horses at 450 kg body weight 20 grams per day. A loading dose for a period of up to ten days of 100 g/d may be required.

Each 20.2 g of Example RE includes:

| | |
|---|---|
| MSM (dimethyl sulfone) | 3 g |
| Acetovanillone (apocynin) | 1 g |
| Phosphatidyl choline (lecithin) | 0.5 g |
| Ginkgo biloba (leaf) | 2 g |
| Ginkgo biloba (standardised extract: | |
| 22% ginkgo flavone glycosides) | 0.1 g |
| Picrorrhiza kurroa | 1 g |
| the balance being herbal extracts and vitamins. | |

It will be appreciated that other compositions are within the scope of the invention.

The invention claimed is:

1. A pharmaceutical composition comprising a unitary dose of *ginkgo biloba* equivalent to between 1 mg/kg bodyweight and 25 mg/kg body weight *ginkgo biloba*, standardized to 24% *ginkgo* flavone glycosides, and a unitary dose of apocynin of between 60 µg/kg body weight and 20 mg/kg body weight.

2. A composition including apocynin, *picrorrhiza kurroa*, standardized to a minimum of 2% Kutkin; lactoferrin; *ginkgo biloba*, standardized to 18% *ginkgo* flavone glycosides; bee pollen; *chlorella pyrenoidosa*; phosphatidylcholine; and *fucus vesiculosus* in the parts by weight ratio of 100:200:60:150:120:250:100:20.

3. A composition including apocynin, *picrorrhiza kurroa*, standardized to a minimum of 2% Kutkin; *ginkgo biloba*, standardized to 24% *ginkgo* flavone glycosides; *chlorella pyrenoidosa*; and phosphatidylcholine in the parts by weight ratio of 180:360:260:100:100.

4. A composition including apocynin, *picrorrhiza kurroa*, standardized to a minimum of 2% Kutkin; lactoferrin; *ginkgo biloba*, standardized to 24% *ginkgo* flavone glyco-sides; bee pollen; *chlorella pyrenoidosa*; phosphatidylcholine; and *fucus vesiculosus* in the parts by weight ratio of 100:200:150:100:280:150:20.

5. A method of treating or preventing an inflammatory disease, thrombosis, cardiac problems and/or conditions caused by platelet induced blood clotting, in a human or non-human animal subject, which comprises the step of administering to the subject the pharmaceutical composition of claim 1.

6. A method of treating or preventing an inflammatory disease, thrombosis, cardiac problems and/or conditions caused by platelet induced blood clotting, in a human or non-human animal subject, which comprises the step of administering to the subject the pharmaceutical composition of claim 2.

7. A method of treating or preventing an inflammatory disease, thrombosis, cardiac problems and/or conditions caused by platelet induced blood clotting, in a human or non-human animal subject, which comprises the step of administering to the subject the pharmaceutical composition of claim 3.

8. A method of treating or preventing an inflammatory disease, thrombosis, cardiac problems and/or conditions caused by platelet induced blood clotting, in a human or non-human animal subject, which comprises the step of administering to the subject the pharmaceutical composition of claim 4.

9. A method of treating or preventing an inflammatory disease in a human or a non-human animal subject comprising the step of administering to the subject the pharmaceutical composition of claim 1.

10. A method of treating or preventing an inflammatory disease in a human or a non-human animal subject comprising the step of administering to the subject the pharmaceutical composition of claim 2.

11. A method of treating or preventing an inflammatory disease in a human or a non-human animal subject comprising the step of administering to the subject the pharmaceutical composition of claim 3.

12. A method of treating or preventing an inflammatory disease in a human or a non-human animal subject comprising the step of administering to the subject the pharmaceutical composition of claim 4.

13. A kit containing a preparation for treating or preventing an inflammatory disease, thrombosis, cardiac problems and/or conditions caused by platelet induced blood clotting in a human or non-human animal subject, comprising at least one dose of the pharmaceutical composition of claim 1.

14. A kit containing a preparation for treating or preventing an inflammatory disease, thrombosis, cardiac problems and/or conditions caused by platelet induced blood clotting in a human or non-human animal subject, comprising at least one dose of the pharmaceutical composition of claim 2.

15. A kit containing a preparation for treating or preventing an inflammatory disease, thrombosis, cardiac problems and/or conditions caused by platelet induced blood clotting in a human or non-human animal subject, comprising at least one dose of the pharmaceutical composition of claim 3.

16. A kit containing a preparation for treating or preventing an inflammatory disease, thrombosis, cardiac problems and/or conditions caused by platelet induced blood clotting in a human or non-human animal subject, comprising at least one dose of the pharmaceutical composition of claim 4.

17. A method of dose sparing a therapeutic agent in a human or non-human animal subject comprising the step of administering to the subject the pharmaceutical composition of claim 1.

18. A method of dose sparing a therapeutic agent in a human or non-human animal subject comprising the step of administering to the subject the pharmaceutical composition of claim 2.

19. A method of dose sparing a therapeutic agent in a human or non-human animal subject comprising the step of administering to the subject the pharmaceutical composition of claim 3.

20. A method of dose sparing a therapeutic agent in a human or non-human animal subject comprising the step of administering to the subject the pharmaceutical composition of claim 4.

* * * * *